United States Patent [19]

Munayyer et al.

[11] Patent Number: 5,422,361
[45] Date of Patent: Jun. 6, 1995

[54] STABLE CREAM AND LOTION BASES FOR LIPOPHILIC DRUG COMPOSITIONS

[75] Inventors: Farah J. Munayyer, West Caldwell, N.J.; Joel A. Sequeira, New York, N.Y.

[73] Assignee: Schering Corporation, Kenilworth, N.J.

[21] Appl. No.: 859,494

[22] PCT Filed: Dec. 14, 1990

[86] PCT No.: PCT/US90/07228
§ 371 Date: Jun. 12, 1992
§ 102(e) Date: Jun. 12, 1992

[87] PCT Pub. No.: WO91/08733
PCT Pub. Date: Jun. 27, 1991

Related U.S. Application Data

[63] Continuation of Ser. No. 453,564, Dec. 20, 1989, abandoned.

[51] Int. Cl.$^6$ ............... A61K 31/415; A61K 31/40
[52] U.S. Cl. ............................... 514/408; 514/396; 514/418; 514/419; 514/423; 514/424; 514/887; 514/937; 514/938
[58] Field of Search ............... 514/396, 408, 887, 418, 514/419, 423, 937, 938

[56] References Cited

U.S. PATENT DOCUMENTS

| | | | |
|---|---|---|---|
| 4,039,664 | 8/1977 | Stoughton et al. | 514/947 X |
| 4,316,893 | 2/1982 | Rajadhyaksha | 424/180 |
| 4,424,234 | 1/1984 | Alderson et al. | 424/317 |
| 4,537,776 | 8/1985 | Cooper | 514/424 |

FOREIGN PATENT DOCUMENTS 0131228 1/1985 European Pat. Off.
0245126 11/1987 European Pat. Off.

OTHER PUBLICATIONS

Chemical Abstracts (1977) vol. 87: 157098g (Vazquez et al.).
Chemical Abstracts (1991) vol. 105: 30084j (Naito).

*Primary Examiner*—Marianne M. Cintins
*Assistant Examiner*—T. J. Criares
*Attorney, Agent, or Firm*—Thomas D. Hoffman

[57] ABSTRACT

A cosmetically elegant, physically and chemically stable base in the form of an oil-in-water emulsion for use in cream and lotion lipophilic drug containing- pharmaceutical compositions containing at least one lipophilic drug and an effective amount of N-methyl-2-pyrrolidone is disclosed.

10 Claims, No Drawings

STABLE CREAM AND LOTION BASES FOR LIPOPHILIC DRUG COMPOSITIONS

The present application is the United States national application corresponding to International Application No. PCT/US90/07228, filed 14 Dec. 1990, and designating the United States, which PCT application is in turn a continuation of U.S. application Ser. No. 07/453,564, filed 20 Dec. 1989, now abandoned, the benefit of which applications is claimed pursuant to the provisions of 35 U.S.C. §§120, 363 and 365(C).

This invention relates to cosmetically elegant, chemically and physically stable topical cream and lotion bases and lipophilic drug compositions containing an amount of N-methyl-2-pyrrolidone effective to enable penetration through the skin of lipophilic drugs, such as steroids and antimicrobials.

Topical application of drugs is the preferred mode of administration in many instances to avoid side effects often found with systemic application of such drugs. Topical pharmaceutical compositions should possess the following characteristics:

1) superior skin penetration with minimal skin irritation and/or sensitization;
2) chemical stability;
3) physical stability; and
4) cosmetic elegance.

One of the most serious problems which must be overcome in developing an effective topical base for a pharmaceutical composition is penetration of the drug into the skin. Good skin penetration is a particularly difficult problem for lipophilic drugs exhibiting low water solubility, such as steroids and antimicrobials, especially antifungals and pentrants for such drugs are often added to lipophilic drug-containing compositions.

Penetrants for drugs are known. U.S. Pat. No. 3,551,554 discloses use of dimethyl sulfoxide and U.S. Pat. No. 4,316,893 discloses use of 1-lower alkyl substituted azacyclopentan-2-ones to enhance percutaneous adsorption of drugs. N-methyl-2-pyrrolidone is also a known penetrant for drugs, but it has been found in our laboratories that N-methyl-2-pyrrolidone breaks down emulsion systems such as creams and lotions. Thus, we are aware of no successful cream or lotion systems containing N-methyl-2-pyrrolidone. Creams and lotions, e.g., oil-in-water emulsions, are particularly desirable bases for such lipophilic drugs. In the course of developing the bases and pharmaceutical compositions of the present invention, we prepared numerous creams containing known drug penetration agents such as dimethyl sulfoxide and N-methyl pyrrolidone, but most of these creams did not have all of the desired characteristics necessary for an acceptable topical pharmaceutical formulation for a lipophilic drug.

Thus, there is still a need for a chemically and physically stable, cosmetically elegant topical cream and/or lotion base for a lipophilic drug-containing pharmaceutical composition which allows effective penetration of the lipophilic drug through the skin with minimal skin irritation and/or sensitization.

SUMMARY OF THE INVENTION

We have surprisingly discovered that a chemically and physically stable, cosmetically elegant topical cream and lotion base for lipophilic drug-containing pharmaceutical compositions which incorporates an amount of N-methyl-2-pyrrolidone effective to allow penetration of a lipophilic drug through the skin with minimal skin irritation. Thus, this invention provides a base in the form of an oil-in-water emulsion for use in cream and lotion lipophilic drug-containing pharmaceutical compositions containing at least one lipophilic drug comprising (a) an amount of N-methyl-2-pyrrolidone effective to enable a lipophilic drug to penetrate through the skin, (b) an aqueous phase comprising water and an amount of propylene glycol sufficient to at least partially solibilize a lipophilic drug in the aqueous phase; and (c) an oil phase comprising an amount of mineral oil or diethyl sebacate effective to at least partially solubilize a lipophilic drug in the oil phase, (d) an amount of a surfactant system effective to stablize the emulsion formed from the oil phase and aqueous phase, (e) an occlusive agent, (f) a preservative, and optionally a silicon oil and wherein the pH of said base is in the range of about 4.0 to 7.0.

This invention also provides a topical cream and/or lotion pharmaceutical composition in the form of an oil-in-water emulsion containing at least one lipophilic drug and a base comprising (a) an amount of N-methyl-2-pyrrolidone effective to enable a lipophilic drug to penetrate through the skin, (b) an aqueous phase comprising water and an amount of propylene glycol sufficient to at least partially solubilize a lipophilic drug in the aqueous phase; and (c) an oil phase comprising an amount of diethyl sebacate or mineral oil effective to at least partially solubilize a lipophilic drug in the oil phase; (d) an amount of a surfactant system effective to stabilize the emulsion formed from the oil phase and aqueous phase; (e) an occlusive agent; and (f) a preservative, and wherein the pH of the composition is in the range of about 4.0 to 7.0.

DETAILED DESCRIPTION OF THE INVENTION

In a preferred aspect of the invention, there is provided a base in the form of an oil-in-water emulsion for use in a cream lipophilic drug-containing pharmaceutical composition comprising:

(a) about 25 to 100 mg/g of N-methyl-2-pyrrolidone;
(b) about 20 to 90 mg/g of diethyl sebacate or mineral oil;
(c) about 300 to 700 mg/g of purified water;
(d) about 20 to 120 mg/g of propylene glycol;
(e) about 15 to 65 mg/g of propylene glycol stearate;
(f) about 30 to 75 mg/g of a mixture of stearyl alcohol and ceteareth-20;
(g) about 100 to 200 mg/g of white petrolatum;
(h) about 5 to 15 mg/g of benzyl alcohol; and
(i) about 5 to 20 mg/g of trimethylsiloxy-silicate; and wherein the pH of said base is adjusted to about 4.5 to about 6.5.

In another preferred aspect of this invention, there is provided a base for use in a lotion lipophilic-drug containing pharmaceutical composition in the form of an oil-in-water emulsion comprising:

(a) about 25 to 100 mg/g of N-methyl pyrrolidone;
(b) about 20 to 90 mg/g of diethyl sebacate or mineral oil;
(c) about 300 to 700 mg/g of purified water;
(d) about 20 to 120 mg/g of propylene glycol;
(e) about 15 to 65 mg/g of propylene glycol stearate;
(f) about 30 to 75 mg/g of a mixture of stearyl alcohol and ceteareth-20;
(g) about 50 to 100 mg/g of white petrolatum;
(h) about 5 to 15 mg/g of benzyl alcohol; and (i) about 5 to 20 mg/g of trimethylsiloxy-silicate; and wherein the pH of the purified water-containing phase is adjusted to about 5.5 to about 6.5.

In another preferred aspect, this invention provides a topical cream and lotion pharmaceutical composition in the form of an oil-in-water emulsion for application of a lipophilic drug to the skin comprising:
(a) about 0.5 to 20 mg/g of at least one lipophilic drug;
(b) about 20 to 90 mg/g of diethyl sebacate or mineral oil;
(c) about 50 to 200 mg/g of white petrolatum;
(d) about 15 to 65 mg/g of propylene glycol stearate;
(e) about 35 to 70 mg/g of a mixture of stearyl alcohol and ceteareth-20;
(f) about 5 to 20 mg/g of a trimethylsiloxy-silicate;
(g) about 300 to 800 mg/g of purified water;
(h) about 20 to 120 mg/g of propylene glycol; and
(i) about 25 to 100 mg/g of N-methyl-2-pyrrolidone; and wherein the pH of said composition is adjusted to a value in the range of about 4.5 to 6.5

In still another aspect, this invention provides a topical cream pharmaceutical composition in the form of an oil-in-water emulsion for treatment of inflammation comprising:
(a) about 0.5 to 1.5 mg/g of a lipophilic steroid drug selected from mometasone furoate, betamethasone diprorionate, betamethasone valerate alcolomethasone diprorionate, hydrocortisone and mixtures thereof;
(b) about 20 to 90 mg/g of diethyl sebacate or mineral oil;
(c) about 100 to 200 mg/g of white petrolatum;
(d) about 15 to 65 mg/g of propylene glycol strearate;
(e) about 30 to 75 mg/g of a 75:25 (w/w) mixture of stearyl alcohol and ceteareth-20;
(f) about 5 to 20 mg/g of trimethylsiloxy-silicate;
(g) about 300 to 700 mg/g of purified water;
(h) 20 to 120 mg/g of propylene glycol; and
(i) about 5 to 15 mg/g of benzyl alcohol; and
(j) about 25 to 100 mg/g of N-methyl-2-pyrrolidone; and wherein the pH of said composition is adjusted to a value in the range of about 4.5 to 6.5.

In a further aspect, this invention provides a topical lotion pharmaceutical composition in the form of an oil-in-water emulsion for treatment of inflammation comprising:
(a) about 0.5 to about 1.5 mg/g of a lipophilic steroid drug selected from mometasone furoate, betamethasone diprorionate, betamethasone valerate alcomethasone diprorionate, hydrocortisone and mixtures thereof;
(b) about 20 to 90 mg/g of diethyl sebacate or mineral oil;
(c) about 50 to 100 mg/g of white petrolatum;
(d) about 15 to 65 mg/g of propylene glycol stearate;
(e) about 30 to 75 mg/g of a 75:25 (w/w) mixture of stearyl alcohol and ceteareth-20;
(f) about 5 to 20 mg/g of trimethylsiloxy-silicate;
(g) about 400 to 800 mg/g of purified water;
(h) about 20 to 120 mg/g of propylene glycol;
(i) about 5 to 15 mg/g of benzyl alcohol; and
(j) about 25 to 100 mg/g of N-methyl-2-pyrrolidone; and wherein the pH of said composition is adjusted to a value in the range of about 4.5 to 6.5.

In another preferred aspect of the present invention the provision provides a topical cream pharmaceutical composition in the form of an oil-in-water emulsion for treatment of inflammation comprising:
(a) about 5. to 15 mg/g of a lipophilic antifungal drug;
(b) about 20 to 90 mg/g of diethyl sebacate or mineral oil;
(c) about 100 to 200 mg/g of white petrolatum;
(d) about 15 to 65 mg/g of propylene glycol stearate;
(e) about 30 to 75 mg/g of a mixture of stearyl alcohol and Cetreareth-20;
(f) about 5 to 20 mg/g of trimethylsiloxy-silicate;
(g) about 300 to 700 mg/g of purified water;
(h) about 20 to 120 mg/g of propylene glycol;
(i) about 5 to 15 mg/g of benzyl alcohol; and
(j) about 25 to 100 mg/g of N-methyl-2-pyrrolidone; and wherein the pH of said composition is adjusted to a value in the range of about 4.5 to about 6.5.

The preferred lipophilic antifungal agents are clotrimazole and tolnaftate.

In still another preferred aspect, this invention provides a topical lotion pharmaceutical composition in the form of an oil-in-water emulsion for treatment of inflammation comprising:
(a) about 5 to 15 mg/g of a lipophilic antifungal agent;
(b) about 20 to 90 mg/g of diethyl sebacate or mineral oil;
(c) about 50 to 100 mg/g of white petrolatum;
(d) about 15 to 65 mg/g of propylene glycol stearate;
(e) about 30 to 75 mg/g of a mixture of stearyl alcohol and Ceteareth-20;
(f) about 5 to 20 mg/g of trimethylsiloxy-silicate;
(g) about 400 to 800 mg/g of purified water;
(h) about 20 to 120 mg/g of propylene glycol;
(i) about 5 to 15 mg/g of benzyl alcohol; and
(j) about 25 to 100 mg/g of N-methyl-2-pyrrolidone; and wherein the pH of said composition is adjusted to a valve in the range of about 4.5 to about 6.5.

The preferred antifungal agents are clotrimazole and tolnaftate.

The topical cream bases and topical cream pharmaceutical composition preferably contain about 400 to about 700 mg/g of purified water.

We have surprisingly discovered that N-methyl-2-pyrrolidone (herein after M-pyrol) which has been found by us to disrupt cream structures by causing a breakdown of the emulsion can be successfully used in a cream or lotion base to promote the enhancement of skin penetration of lipophilic drugs without causing a breakdown in the emulsion. The present invention provides unique oil-in-water cream and lotion bases which possess a high degree of cosmetic elegance compared to other conventional cream bases. Even though the bases of the present invention incorporate M-pyrol as the penetrant for lipophilic drugs, the bases and pharmaceutical compositions of the present invention are physically and chemically stable at elevated temperature for periods as long as 3 months to 2 years while simultaneously providing support skin penetration for a variety of lipophilic drugs.

The term "lipophilic drug" as used herein includes steroids, anti-inflammatory agents, antifungal agents and carthartic agents.

Typical suitable steroids include mometasone furoate, betamethasone and its esters especially betamethasone diprorionate, betamethasone valerate and betamethasone divalerate, alcolomethasone, and its esters, especially alcolomethasone diprorionate as well as other lipophilic physiologically active steroids which are well known to those skilled in the art.

The pharmaceutical compositions of the present invention incorporating lipophilic steroids are useful for treating inflammatory conditions.

The preferred steroids for use in the pharmaceutical compositions of the invention for treating inflammation includes about 0.5 to 1.5 mg/g of a lipophilic steroid drug selected from mometasone furoate, betamethasone diproprionate, betamethasone valerate, alcolomethasone diproprionate, hydrocortisone and mixtures thereof.

The pharmaceutical compositions of the present invention are also useful for treating mild eczema, for example, by applying a cream or lotion of anti-inflammatory agents such as fluocinolone acetonide or its derivatives, hydrocortisone, triamcinolone acetonide, indomethacin, salicylates or phenylbutazone dispersed in bases of the present invention to the affected area.

Lipophilic antifungal agents such as, for example, clotrimazole and as well as other lipophilic antifungal agents well known to those skilled in the art which may be dispersed in the vehicles described herein and topically applied to affected areas of the skin. For example, antifungal agents so applied are carried into the skin to the location of the fungus causing the infection, and thereby successfully treat fungus-caused skin problems. These agents, thus applied, not only penetrate more quickly than when applied in the vehicles of the prior art, but additionally enter the animal tissue in high concentrations and are retained for substantially longer time periods whereby a far more successful treatment is effected.

For example, the pharmaceutical compositions of the present invention may also be employed in the treatment of fungus infections on the skin caused by Candida and dermatophytes which cause athletes foot or ringworm, by dispersing tolnaftate or similar lipophilic antifungal agents such as clotrimazole in a base of the present invention and applying it to the affected area.

The pharmaceutical compositions of the present invention are also useful in treating skin problems, such as for example, herpes simplex, which may be treated by a solution of iododeoxyuridine dispersed in a base of the present invention, or such problems as warts which may be treated with carthartic agents such as podophylline dissolved in one of the bases of this invention. Skin problems such as psoriasis may be treated by topical application of a cream or lotion of a conventional topical steroid in one of the bases of this invention or by treatment with theophylline or antagonists of beta-adrenergic blockers such as isoproterenol in one of the bases of the present invention. Scalp conditions such as alopecia areata may be treated more effectively by applying lipophilic steroids such as triamcinolone acetonide dispersed in one of the bases of this invention directly to the scalp.

The amount of M-pyrol found effective to enable an effective amount of a lipophilic drug to penetrate through the skin is in the range of about 5 to about 15 preferably about 5 to about 10% and more preferably about 5% by weight of the pharmaceutical composition.

The oil phase contains an effective amount of diethyl sebacate or mineral oil. Surprisingly, we found that use of diethyl sebacate or mineral oil in the amount of about 20 to 90 mg/g, preferably an amount of about 35 mg/g of the bases or pharmaceutical compositions of the present invention allowed use of lower amounts (e.g., about 5-10, more preferably about 5 weight %) of M-pyrol. The use of the diethyl sebacate is preferred.

Typical suitable surfactant systems found effective to stabilize the oil-in-water emulsions formed by the oil phase and aqueous phase of the bases and pharmaceutical compositions of the present invention include about 30 to 75 mg/g of a mixture of stearyl alcohol and ceteareth-20 in combination with about 15 to 65 mg/g of a nonionic surfactants selected from propylene glycol stearate, glyceryl monostearate, PEG-1000 monocetyl ether, glyceryl monostearate, sorbitan monostearate and polysorbate-60. Use of about 15-65 mg/g, preferably about 40 mg/g of propylene glycol stearate in combination with about 30-75 mg/g, preferably about 55 mg/g of a of stearyl alcohol and ceteareth-20 mixture of stearyl alcohol and ceteareth-20 is available from Amerchol Corp, Edison N.J. 08812 under the tradename, Promulgen G) as the surfactant system is preferred.

Typical suitable preservatives include benzyl alcohol, potassium sorbate, sorbic acid and sodium benzoate as well as other preservatives, e.g. the paraben, e.g. methylparaben which are normally added to the aqueous phase. Use of about 5 to about 15 mg/g, preferably about 10 mg/g of benzyl alcohol is preferred.

Silicon oils may be incorporated into the formulations of the present invention to enhance cosmetic elegance, especially to provide a cream with a so-called vanishing cream-like appearance to the bases and pharmaceutical compositions of the present invention. Typical suitable silicon oils include silicon oils approved for use in cosmetics and pharmaceuticals. The preferred silicon oil for the present invention is dimethicone (which is a mixture of fully methylated linear siloxane polymers and blocked with trimethylsiloxy units and has the common name "trimethylsiloxy-silicate") in an amount of about 5 to about 20 mg/g, preferably about 10 mg/g of the bases and pharmaceutical composition of the present invention.

The pH of the pharmaceutical composition of the present invention may be in the range of about 4.0 to about 7.0, and the precise pH range depends upon the lipophilic drug or drugs present. Thus, the preferred pH range is (a) about 5.5 to 6.5 when only a lipophilic antifungal such as clotrimazole is present; (b) about 4.0 to 5.0 when a lipophilic steroid such mometasone furoate is present; and (c) in the range of about 4.5 to 6.5, more preferably about 5.5 to 6.5 and most preferably about 6.0 when a mixture of a lipophilic steroid such as mometasone furoate and a lipophilic antifungal such as clotrimazole is present.

Typical suitable buffer systems which maintain the pH of the bases and pharmaceutical compositions of the present invention in the range of 5.5 to 6.5 include sodium phosphate monobasic/sodium phosphate dibasic, and citrate-phosphate.

The bases are emulsions for use in a cream and/or lotion pharmaceutical compositions which are also in the form of emulsions of the present invention as well as the pharmaceutical compositions of the present invention. Such bases and compositions are manufactured in a conventional manner by thoroughly mixing the ingredients at ambient or elevated temperatures. Preferably the lipophilic drug or mixtures of lipophilic drugs are added to a small portion of the emulsion of the oil and water phases. The ingredients are thoroughly mixed so that the product is homogeneous. Processing equipment suitable for preparing the cream are known in the art and include colloid mills, homogenizers, roller mills, propeller mixers and the like.

General Experimental

All ingredients are U.S.P. grade and all percentages are by weight. Definitions of components whose chemical composition is not immediately clear from the name used, such as "Ceteareth-20" and "Promulgen-G", may be found in the CTFA Cosmetic Ingredients Dictionary, 3rd Edition, published by Cosmetic Toiletry and Fragrance Association, Inc., Washington, D.C.

The following examples illustrate the bases and compositions of the present invention. It will be apparent to those skilled in the art that many modifications thereof may be practical without departing from the purpose and intent of this invention.

DESCRIPTION OF TEST PROCEDURES

1. Physical Stability

Samples of the formulations were evaluated initially and/or after being stored at 35° C. or 40° C. for short periods of time e.g., up to 4 weeks by measuring for the following parameters:

(1) breakdown of the emulsion system (separation into separate layers);
(2) color change;
(3) change in viscosity;
(4) change in visual appearance.

Only formulations which did not separate (initially or after short periods) at elevated temperatures of 35° C. or 40° C. into separate layers or did not exhibit a change in color or viscosity or visual appearance were considered physically stable.

2. Vasoconstrictor Scores

The local anti-inflammatory activity of the steroid-containing pharmaceutical compositions of the present invention were tested by the vasoconstrictor assay described by McKenzie and Stoughton, *Arch. Dermatol.*, (1962) Vol. 86, 608.

Sixteen (16) to thirty-two (32) subjects from a pool of healthy volunteers who met certain selection criteria were selected for each study. No individual was used more frequently than once every two weeks.

Four sites, each approximately 2 cm in diameter and at least 1 cm apart, were delineated on the flexor surface of each of the subject's forearms, giving a total number of eight sites per subject. Ten (10) mg of each of the formulations tested per study were randomnly applied to these sites, an equal number of times.

The four sites on each arm were then covered with a protective plastic shield. Six and one half hours later the shields were removed, the test sites were washed with soap and water. Approximately ½ and 18 hours after removal of the shields, (7 and 24 hours after initial application of the test materials), the sites were examined and the degree of blanching (vasoconstriction) was rated as follows: No blanching—0; mild blanching—1; moderate blanching—2 and strong blanching—3.

EXAMPLE 1

This example illustrates the effect of various known drug penetration enhancers (dimethyl sulfoxide, triacetin, solketal, M-pyrol and oleyl alcohol) to enhance the skin penetration of mometasone furoate present in various cream bases.

| Ingredients | mg/g |
|---|---|
| BASE A | |
| Mometasone Furoate, Micronized | 1 |
| Propylene Glycol USP | 100 |
| Drug Penetration Enhancers* | 100 |
| Mineral Oil USP | 60 |
| White Petrolatum USP | 150 |
| Cetostearyl Alcohol NF | 72 |
| PEG-1000, Monocetyl Ether | 22.5 |
| Benzyl Alcohol | 10 |
| Sodium Phosphate Monobasic Monohydrate USP | 2.65 |
| Phosphoric Acid NF | 0.62 |
| Water Purified USP   q.s. | 481.83 |
| BASE B | |
| Mometasone Furoate Micronized | 1 |
| Olive Oil | 200 |
| Oleyl Alcohol** | 50 |
| Propylene Glycol USP | 100 |
| Isopropyl Myristate | 10 |
| White Petrolatum USP | 150 |
| Stearyl Alcohol and Ceteareth-20 | 80 |
| PEG-1000, Monocetyl Ether | 24 |
| Sodium Phosphate Monobasic Monohydrate USP | 2.65 |
| Phosphoric Acid NF | 0.02 |
| Water Purified USP   q.s. | 382.33 |
| DIPROSONEG Ointment, 0.05%[1] | |
| Betamethasone diproprionate, Micronized | 0.64*** |
| Mineral Oil, USP | 50.00 |
| White Petrolatum, USP | 949.36 |
| | 1.0 g |

*dimethylsulfoxide, triacetin, solketal, M-pyrol.
**Drug Penetrant
***Equivalent to 0.5 mg/g of Betamethasone
[1]Available from Schering-Plough Corporation, Kenilworth, New Jersey.

The five formulations containing the five drug penetration enhancers listed above were evaluated for vasoconstrictor activity, cosmetic elegance and physical stability and compared to those for DIPROSONE Ointment. The results are reported in the following Table I.

TABLE I

| Drug Penetrant | 7 Hrs. Vasoconstrictor Score[1] | Cosmetically Elegant | Physically Stability |
|---|---|---|---|
| Dimethyl Sulfoxide* | 59 | une;egant | unstable |
| Triacetin* | 69 | " | " |
| Solketal* | 29 | " | " |
| M-pyrol* | 98 | " | " |
| Oleyl Alcohol** | 44 | " | " |
| Diprosone Ointment, 0.05% | 100 | elegant | stable |

[1]Mean score of 24 subjects; expressed as a % of Diprosone Ointment, 0.05%.
*in Base A
**in Base B

EXAMPLE 2

This example illustrates effect of the variation of M-pyrol concentration in a base containing mineral oil on the vasoconstrictor activity

| Ingredients | mg/g |
|---|---|
| FORMULATION 2A (5% M-pyrol) | |
| Mometasone Furoate, Micronized | 1 |
| Mineral Oil USP | 60 |
| Propylene Glycol USP | 100 |
| M-pyrol | 50 |
| White Petrolatum USP | 150 |
| Cetostearyl Alcohol NF | 72 |
| Benzyl Alcohol | 10 |
| PEG-1000, Monocetyl Ether | 30 |
| Sodium Phosphate Monobasic Monohydrate USP | 2.65 |
| Phosphoric Acid NF | 0.02 |
| Water Purified USP | 524.33 |
| FORMULATION 2B (10% M-pyrol) | |

| Ingredients | mg/g |
|---|---|
| Mometasone Furoate Micronized | 1 |
| Mineral oil USP | 60 |
| Propylene Glycol USP | 100 |
| M-pyrol | 100 |
| White Petrolatum USP | 150 |
| Cetostearyl Alcohol NF | 72 |
| Benzyl Alcohol | 10 |
| PEG-1000, Monocetyl Ether | 30 |
| Sodium Phosphate Monobasic Monohydrate USP | 2.65 |
| Phosphoric Acid NF | 0.02 |
| Water Purified USP | 474.33 |
| FORMULATION 2C (15% M-pyrol) | |
| Ingredients | |
| Mometasone Furoate Micronized | 1 |
| Mineral oil USP | 60 |
| Propylene Glycol USP | 100 |
| M-pyrol | iso |
| White Petrolatum USP | 150 |
| Cetostearyl Alcohol NF | 72 |
| Benzyl Alcohol | 10 |
| PEG-1000, Monocetyl Ether | 30, |
| Sodium Phosphate Monobasic Monohydrate USP | 2.65 |
| Phosphoric Acid NF | 0.02 |
| Water Purified USP | 424.33 |
| FORMULATION 2D (20% M-pyrol) | |
| Mometasone Furoate Micronized | 1 |
| Mineral Oil USP | 60 |
| Propylene Glycol USP | 100 |
| M-pyrol | 200 |
| White Petrolatum USP | 150 |
| Cetostearyl Alcohol NF | 72 |
| Benzyl Alcohol | 10 |
| PEG-1000, Monocetyl Ether | 30 |
| Sodium Phosphate Monobasic Monohydrate USP | 2.65 |
| Phosphoric Acid NF | 0.02 |
| Water Purified USP | 374.33 |

TABLE II
EFFECT OF M-PYROL LEVEL ON VASOCONSTRICTOR ACTIVITY

| Formulation | Conc. M-pyrol | 7 Hrs. Vasoconstrictor Score[1] | Cosmetic Elegant | Physical Stability |
|---|---|---|---|---|
| 2A | 5 | 80 | inelegant | unstable |
| 2B | 10 | 86 | " | " |
| 2C | 15 | 100 | " | " |
| 2D | 20 | 82 | " | " |
| ELOCON ® Cream[2] | — | 100 | elegant | stable |

[1]Mean score of 24 subjects; expressed as a % of ELOCON Cream.
[2]Tradename of a mometasone furoate cream, 0.1% available from Schering-Plough Corporation, Kenilworth, NJ.

EXAMPLE 3

This example illustrates the effect of the surfactant system on the cosmetic elegance and physical and chemical stability of a base containing M-pyrol.

| Ingredients | mg/g |
|---|---|
| FORMULATION 3A | |
| Mometasone Furoate, Micronized | 1 |
| Mineral Oil USP | 60 |
| Propylene Glycol USP | 100 |
| M-pyrol | 100 |
| White Petrolatum USP | 150 |
| Cetostearyl Alcohol NF | 72 |
| Benzyl Alcohol | 10 |
| PEG-1000, Monocetyl Ether | 30 |
| Sodium Phosphate Monobasic Monohydrate USP | 2.65 |
| Phosphoric Acid NF | 0.02 |
| Water Purified USP | 474.33 |
| FORMULATION 3B | |
| Mometasone Furoate Micronized | 1 |
| Mineral Oil USP | 60 |
| Propylene Glycol USP | 100 |
| M-pyrol | 150 |
| White Petrolatum USP | 150 |
| Cetostearyl Alcohol NF | 72 |
| Benzyl Alcohol | 10 |
| PEG-1000, Monocetyl Ether | 30 |
| Sodium Phosphate Monobasic Monohydrate USP | 2.65 |
| Phosphoric Acid NF[1] | 0.02 |
| Water Purified USP | 424.33 |
| FORMULATION 3C | |
| Mometasone Furoate Micronized | 0.5 |
| Clotrimazole Micronized | 10 |
| Mineral Oil USP | 60 |
| White Petrolatum #4 USP | 150 |
| Propylene glycol stearate | 40 |
| Stearyl alcohol and Ceteareth-20 | 35 |
| Propylene glycol USP | 100 |
| Benzyl Alcohol | 10 |
| Sodium Phosphate dibasic USP | 0.35 |
| Sodium Phosphate monobasic USP | 5 |
| M-pyrol | 150 |
| Purified Water USP | 439.15 |

Procedure for Preparing Formulations 3A and 3B

1. Charge mineral oil, white petrolatum, cetostearyl alcohol and PEG-1000 monocetyl ether into a suitable jacketted container. Heat the mixture to melt at 65°–70° C.
2. In a separate container, dissolve sodium phosphate monobasic monohydrate and phosphoric acid in water at 65°–70° C.
3. Add benzyl alcohol to the water solution in Step 2 and mix well.
4. At 65°–70° C. charge the aqueous phase (Step 3) to oil phase (Step 1) and mix well to emulsify. Cool to 30°–35° C. with appropriate agitation.
5. Dissolve mometasone furoate into the M-pyrol.
6. Add the mixture Step 5 to that of Step 4 and mix appropriately while cooling to room temperature.

Procedure for Preparing Formulation 3C

1. In a stainless steel bowl, weigh the white petrolatum, propylene glycol stearate, stearyl alcohol and Ceteareth-20 and heat the admixture to melt (65°–70° C.).
2. Disperse mometasone furoate in mineral oil with heat. When it is dissolved, add to Step 1 and mix.
3. Into a separate container, weigh the purified water, propylene glycol, M-pyrol and benzyl alcohol. Heat the admixture to 65°–70° C. with mixing.
4. Add Step 3 to Step 1 and homogenize the batch with appropriate mixing for approximately ten minutes. Start the so-formed emulsion to cool.
5. At 45° C., withdraw an adequate amount of emulsion (Step 4) to slurry clotrimazole in a slurry container and rinse slurry container.
6. Slurry the clotrimazole with a portion of the emulsion from Step 5 and add to the admixture of Step 3. Mix well to disperse.
7. Rinse the slurry container with the remaining portion of emulsion of Step 5 and charge rinses to Step 5. Mix well.
8. Adjust the pH of the so-formed emulsion to 5.9 ±0.1 with phosphate buffer solution.
9. Transfer the emulsion to an appropriate mixer and continue to mix. Cool to RT to form a cream.
10. Fill the cream into the appropriate packages.

Formulations 3A to 3C were compared to ELO-CON ® Cream as described above. The results are reported in Table III.

TABLE III
EFFECT OF M-PYROL LEVEL ON VASOCONSTRICTOR ACTIVITY

| Formulation | M-pyrol % | 7 Hrs. Vaso-constrictor Score[1] | Cosmetic Elegant | Physical Stability |
|---|---|---|---|---|
| 3A | 10 | 115 | inelegant | unstable |
| 3B | 15 | 111 | " | " |
| 3C[2] | 15 | 90[2] | elegant | stable |
| ELOCON ® Cream 0.1% | — | 100 | " | " |

[1] Mean score of 24 subjects; expressed as a % of Elocon Cream, 0.1%.
[2] Lower Vasoconstrictor score due to fact that Formulation 3C contained only ½ the amount of clotrinazole present in Formulations 3A and 3B.

EXAMPLE 4

This example provides two cream formulations containing mineral oil and exhibiting high vasoconstrictor scores, which formulation, however, were physically unstable.

| Ingredients | mg/g |
|---|---|
| CREAM FORMULATION 4A | |
| Mometasone Furoate Micronized | 0.5 |
| Clotrimazole Micronized | 10 |
| Mineral Oil USP | 60 |
| White Petrolatum #4 USP | 150 |
| Propylene glycol stearate | 40 |
| Stearyl alcohol and Ceteareth-20 | 35 |
| Propylene glycol USP | 100 |
| Benzyl Alcohol | 10 |
| Sodium Phosphate Monobasic USP | 2.65 |
| N-Methyl-2-Pyrrolidone (M-pyrol) | 150 |
| Purified Water USP | 441.85 |
| CREAM FORMULATION 4B | |
| Mometasone Furoate Micronized | 1 |
| Mineral Oil USP | 60 |
| White Petrolatum #4 USP | 150 |
| Propylene Glycol Stearate | 40 |
| Stearyl alcohol and Ceteareth-20 | 35 |
| Propylene glycol USP | 100 |
| Benzyl Alcohol NF | 10 |
| Phosphoric Acid NF | 0.02 |
| Sodium Phosphate Monobasic USP | 2.65 |
| N-Methyl-2-Pyrrolidone (M-pyrol) | 150 |
| Purified Water USP | 451.33 |

Procedure

1. Charge white petrolatum, propylene glycol stearate, stearyl alcohol and Ceteareth-20, into a suitable jacketed container. Heat the materials to 65°-70° C. while mixing.
2. Charge purified water, propylene glycol, N-methyl-2-pyrrolidone and benzyl alcohol into a suitable jacketed container. Heat the mixture to 65°-70° C. while mixing.
3. Charge the mixture of Step 2 to the mixture of Step 1. Mix with an appropriate homogenizer for about 10 minutes. Check the pH. If necessary, adjust pH to 5.6 ±0.1 with a 1% (w/v) solution of either phosphoric acid or sodium hydroxide. While mixing the batch, cool the batch to 30°-35° C.
4. Remove an adequate amount of the emulsion of Step 3 and charge it into an appropriate container. Mix the emulsion with the clotrimazole micronized, and mometasone furoate micronized to form a slurry.
5. Add the slurry to the batch of Step 3. While mixing, the so-formed batch maintain the batch at approximately 30° C.
6. Check the pH of the batch. If necessary, adjust pH to 5.9 ±0.2 with a 1% (w/v) solution of either phosphoric acid or sodium hydroxide. Bring the batch to final weight with purified water. Mix until homogeneous.
7. Cool the batch to room temperature (approximately 25° C.).

Cream formulations 4A and 4B were evaluated compared to ELOCON ® Cream containing 0.1% mometasone furoate in accordance with procedures of Examples 1–3. The results are provided in Table IV.

TABLE IV

| Formulation | M-Pyrol (%) | 7 Hrs. Vasoconstrictor Score* |
|---|---|---|
| 4A** | 15 | 87** |
| 4B** | 15 | 110** |
| ELOCON ® Cream 0.1% | — | 100 |

*Mean score of 24 subjects; expressed as a % of ELOCON Cream, 0.1%.
**Physical unstable at 35° C. after 1 month.

EXAMPLE 5

This example illustrates various preferred cream bases of the present invention containing diethyl sebacate.

| Ingredient | mg/g | Range mg/g |
|---|---|---|
| Diethyl Sebacate | 35 | 20–90 |
| White Petrolatum #4 | 150 | 100–200 |
| Propylene glycol stearate | 40 | 15–65 |
| Stearyl alcohol & Ceteareth-20* | 55 | 30–75 |
| Propylene glycol | 50 | 20–120 |
| Benzyl alcohol | 10 | 5–15 |
| Sodium phosphate monobasic | 1.5* | * |
| Sodium phosphate dibasic | 0.1* | * |
| Trimethylsiloxy silicate | 10 | 5–20 |
| N-Methyl-2-Pyrrolidone (M-pyrol) | 50 | 25–100 |
| Purified Water q.s. | 1 g | 300–700 |

*PROMULGEN-G

Method of Manufacture

1. In a stainless steel bowl, weight the white petrolatum, propylene glycol stearate, diethyl sebacate, stearyl alcohol and ceteareth-20 and trimethylsiloxy silicate. Heat the mixture to melt (65°–70° C.).
2. Into a separate container, weigh the purified water, propylene glycol, N-methyl-2-pyrrolidone and benzyl alcohol. Heat the mixture to 65°–70° C. with mixing.
3. Add Step 2 to Step 1 and homogenize the batch with appropriate mixing for approximately ten minutes.
4. Adjust pH to 5.9 ±0.2 with phosphoric acid, or a sodium hydroxide solution.
5. Transfer the batch of step 4 to an appropriate mixer and continue to mix.

EXAMPLE 6

This example illustrates preferred cream and lotion pharmaceutical formulations of the present invention.

| Ingredient | mg/g | Range mg/g |
|---|---|---|
| Vanishing Cream | | |

| Ingredient | mg/g | Range mg/g |
|---|---|---|
| Mometasone Furoate Micronized | 1 | 0.5–1.5 |
| Clotrimazole Micronized | 10 | 5–15 |
| Diethyl Sebacate | 35 | 20–90 |
| White Petrolatum #4 | 150 | 100–200 |
| Propylene glycol stearate | 40 | 15–65 |
| Stearyl alcohol & Ceteareth-20 | 55 | 30–75 |
| Propylene glycol | 50 | 20–120 |
| Benzyl alcohol | 10 | 5–15 |
| Sodium phosphate monobasic | 1.5* | * |
| Sodium phosphate dibasic | 0.1* | * |
| Trimethylsiloxy-silicate | 10 | 5–20 |
| N-Methyl-2-Pyrrolidone (M-pyrol) | 50 | 25–100 |
| Purified Water q.s. | 1 g | 300–700 |
| Lotion | | |
| Mometasone Furoate Micronized | 1 | 0.5–1.5 |
| Clotrimazole | 10 | 5–15 |
| Diethyl sebacate | 35 | 20–90 |
| White Petrolatum #4 | 100 | 50–100 |
| Propylene glycol stearate | 25 | 15–65 |
| Stearyl alcohol & Ceteareth-20 | 25 | 30–75 |
| Propylene glycol | 50 | 20–120 |
| Benzyl alcohol | 10 | 5–15 |
| Trimethylsiloxy silicate | 10 | 5–20 |
| Sodium phosphate monobasic | 1.5* | * |
| Sodium phosphate dibasic | 0.1* | * |
| N-Methyl-2-Pyrrolidone (M-pyrol) | 50 | 25–100 |
| Purified Water q.s. | 1 g | 300–700 |

*Used to adjust pH to 5.9 to ±0.1.

Method of Preparation of Vanishing Cream

1. In a stainless steel bowl, weigh the white petrolatum, propylene glycol stearate, stearyl alcohol & Ceteareth-20, diethyl sebacate and trimethylsiloxy silicate. Heat to melt (65°–70° C.).
2. Into a separate container, dissolve sodium phosphate monobasic and sodium phosphate dibasic in the purified water.
3. Add propylene glycol, N-methyl-2-pyrrolidone and benzyl alcohol to the mixture of step 2. Heat the so-formed mixture to 65°–70° C. with mixing.
4. Add Step 3 to Step 1 and homogenize the batch with appropriate mixing for approximately ten minutes. Cool it to 30° to 35° C.
5. At 30°–35° C., add to step 4. The mometasone furoate and clotrimazole and mix until a homogeneous emulsion is formed and then cool the so-formed emulsion to room temperature.
6. Check pH and if necessary adjust pH to 5.9 ±0.1 with phosphoric acid or sodium hydroxide solution.
7. Transfer to an appropriate mixer and continue to mix until cream emulsion is formed.
8. Fill the cream emulsion into the appropriate packages.

The lotion was formulated in a manner analogous to that of the cream.

The lotion and cream exhibited high vasoconstrictor scores and were cosmetically elegant and physically and chemically stable after storage at 35° and 40° C. for 2 years.

EXAMPLE 7

This example illustrates preferred cream and lotion pharmaceutical formulations of the present invention containing mometasone furoate micronized as a preferred lipophilic steroid and prepared in accordance with the procedure of Example 6 except no clotrimazole was added in step 5. Similar cream and lotion formulations containing betamethasone diproprionate, betamethasone valerate or alcolomethasone diproprionate may be prepared in an analogous manner.

| Ingredient | mg/g | Range mg/g |
|---|---|---|
| Vanishing Cream | | |
| Mometasone Furoate Micronized | 1 | 0.5–1.5 |
| Diethyl Sebacate | 35 | 20–90 |
| White Petrolatum #4 | 150 | 100–200 |
| Propylene glycol stearate | 40 | 15–65 |
| Stearyl alcohol & Ceteareth-20 | 55 | 30–75 |
| Propylene glycol | 50 | 20–120 |
| Benzyl alcohol | 10 | 5–15 |
| Sodium phosphate monobasic | 1.5* | * |
| Sodium phosphate dibasic | 0.1* | * |
| Trimethylsiloxy-silicate | 10 | 5–20 |
| N-Methyl-2-Pyrrolidone (M-pyrol) | 50 | 25–100 |
| Purified Water q.s. | 1 g | 300–700 |
| Lotion | | |
| Mometasone Furoate Micronized | 1 | 0.5–1.5 |
| Diethyl sebacate | 35 | 20–90 |
| White Petrolatum #4 | 100 | 50–100 |
| Propylene glycol stearate | 25 | 15–65 |
| Stearyl alcohol & Ceteareth-20 | 25 | 30–75 |
| Propylene glycol | 50 | 20–120 |
| Benzyl alcohol | 10 | 5–15 |
| Trimethylsiloxy silicate | 10 | 5–20 |
| Sodium phosphate monobasic | 1.5* | * |
| Sodium phosphate dibasic | 0.1* | * |
| N-Methyl-2-Pyrrolidone (M-pyrol) | 50 | 25–100 |
| Purified Water q.s. | 1 g | 300–700 |

*Used to adjust the pH to 4.0 to 5.0.

EXAMPLE 8

This example illustrates preferred cream and lotion pharmaceutical formulations of the present invention containing clotrimazole as the preferred lipophilic antifungal and prepared in accordance with the procedure of Example 6 except that only clotrimazole is added in step 5. A similar cream and lotion formulation could also be prepared by substituting tolnaftate for clotrimazole.

| Ingredient | mg/g | Range mg/g |
|---|---|---|
| Vanishing Cream | | |
| Clotrimazole Micronized | 10 | 5–15 |
| Diethyl sebacate | 35 | 20–90 |
| White Petrolatum #4 | 150 | 100–200 |
| Propylene glycol stearate | 40 | 15–65 |
| Stearyl alcohol & Ceteareth-20 | 55 | 30–75 |
| Propylene glycol | 50 | 20–120 |
| Benzyl alcohol | 10 | 5–15 |
| Sodium phosphate monobasic | 1.5* | * |
| Sodium phosphate dibasic | 0.1* | * |
| Trimethylsiloxy-silicate | 10 | 5–20 |
| N-Methyl-2-Pyrrolidone (M-pyrol) | 50 | 25–100 |
| Purified Water q.s. | 1 g | 300–700 |
| Lotion | | |
| Clotrimazole | 10 | 5–15 |
| Diethyl sebacate | 35 | 20–90 |
| White Petrolatum #4 100 | 50–100 | |
| Propylene glycol stearate | 25 | 15–65 |
| Stearyl alcohol Ceteareth-20* | 25 | 30–75 |
| Propylene glycol | 50 | 20–120 |
| Benzyl alcohol | 10 | 5–15 |
| Trimethylsiloxy silicate | 10 | 5–20 |
| Sodium phosphate monobasic | 1.5* | * |
| Sodium phosphate dibasic | 0.1* | * |
| N-Methyl-2-Pyrrolidone (M-pyrol) | 50 | 25–100 |
| Purified Water q.s. | 1 g | 300–700 |

*Used to adjust pH to 5.5 to 6.5.

EXAMPLE 9

This example illustrates preferred cream and lotion pharmaceutical formulations of the present invention prepared in accordance with the procedure of Example 6 except that mineral oil is added in step 1 in place of diethyl sebacate. Similar cream and lotion formulation could also be prepared by substituting for mometasone furoate another steroid such as betamethasone diproprionate, betamethasone valerate or alcolomethasone diproprionate and substituting for the clotrimzole another antifungal such as tolnaftate

| Ingredient | mg/g | Range mg/g |
|---|---|---|
| Vanishing Cream | | |
| Mometasone Furoate Micronized | 1 | 0.5–1.5 |
| Clotrimazole Micronized | 10 | 5–15 |
| Mineral Oil USP | 35 | 20–90 |
| White Petrolatum #4 | 150 | 100–200 |
| Propylene glycol stearate | 40 | 15–65 |
| Stearyl alcohol & Ceteareth-20 | 55 | 30–75 |
| Propylene glycol | 50 | 20–120 |
| Benzyl alcohol | 10 | 5–15 |
| Sodium phosphate monobasic | 1.5* | * |
| Sodium phosphate dibasic | 0.1* | * |
| Trimethylsiloxy-silicate | 10 | 5–20 |
| N-Methyl-2-Pyrrolidone (M-pyrol) | 50 | 25–100 |
| Purified Water    q.s. | 1 g | 300–700 |
| Lotion | | |
| Mometasone Furoate micronized | 1 | 0.5–1.5 |
| Clotrimazole | 10 | 5–15 |
| Mineral Oil USP | 35 | 20–90 |
| White Petrolatum #4 | 100 | 50–100 |
| Propylene glycol stearate | 25 | 15–65 |
| Stearyl alcohol & Ceteareth-20 | 25 | 30–75 |
| Propylene glycol | 50 | 20–120 |
| Benzyl alcohol | 10 | 5–15 |
| Trimethylsiloxy silicate | 10 | 5–20 |
| Sodium phosphate monobasic | 1.5* | * |
| Sodium phosphate dibasic | 0.1* | * |
| N-Methyl-2-Pyrrolidone (M-pyrol) | 50 | 25–100 |
| Purified Water    q.s. | 1 g | 300–700 |

*Used to adjust pH to 5.5 to 6.5.

Method of Preparation of Vanishing Cream

1. In a stainless steel bowl, weigh the white petrolatum, propylene glycol stearate, stearyl alcohol & Ceteareth-20, mineral oil and trimethylsiloxy silicate. Heat the mixture to melt (65°–70° C.).
2. Into a separate container, dissolve sodium phosphate monobasic and sodium phosphate dibasic in the purified water.
3. Add propylene glycol, N-methyl-2-pyrrolidone and benzyl alcohol to step 2. Heat the mixture to 65°–70° C. with mixing.
4. Add Step 3 to Step 1 and homogenize the batch with appropriate mixing for approximately ten minutes. Cool the batch to 30° to 35° C.
5. At 30°–35° C., add to step 4 the mometasone furoate and clotrimazole and mix until a homogeneous emulsion is formed and then cool the so-formed emulsion to room temperature.
6. Check pH and if necessary adjust pH to 5.9 ±0.1 with phosphoric acid or sodium hydroxide solution.
7. Transfer the emulsion to an appropriate mixer and continue to mix until a cream emulsion is formed.
8. Fill the cream emulsion into the appropriate packages.

The lotion is formulated in a manner analogous to that of the cream emulsion formulations.

The lotion and cream are expected to exhibit high vasoconstrictor scores and to be physically and chemically stable after prolonged storage at 25° and 35° C.

What is claimed is:

1. A topical cream pharmaceutical composition comprising:
   (a) 0.5 to 2.0 mg/g of at least one lipophilic steroid or antifungal drug;
   (b) 20 to 90 mg/g of diethyl sebacate or mineral oil;
   (c) 100 to 200 mg/g of white petrolatum;
   (d) 15 to 65 mg/g of propylene glycol stearate;
   (e) 30 to 75 mg/g of a mixture of stearyl alcohol and Ceteareth-20;
   (f) 5 to 20 mg/g of trimethylsiloxy-silicate;
   (g) 300 to 700 mg/g of purified water;
   (h) 20 to 120 mg/g of propylene glycol;
   (i) 5 to 15 mg/g of benzyl alcohol; and
   (j) 25 to 100 mg/g of N-methyl-2-pyrrolidone;
   and wherein the pH of said composition is adjusted to a value in the range of 4.5 to 6.5.

2. A topical lotion pharmaceutical composition comprising:
   (a) 0.5 to 2.0 mg/g of at least one lipophilic steroid or antifungal drug;
   (b) 20 to 90 mg/g of diethyl sebacate or mineral;
   (c) 50 to 100 mg/g of white petrolatum;
   (d) 15 to 65 mg/g of propylene glycol stearate;
   (e) 30 to 75 mg/g of a mixture of stearyl alcohol and Ceteareth-20;
   (f) 5 to 20 mg/g of trimethylsiloxy-silicate;
   (g) 400 to 800 mg/g of purified water;
   (h) 20 to 120 mg/g of propylene glycol;
   (i) 5 to 15 mg/g of benzyl alcohol; and
   (j) 25 to 100 mg/g of N-methyl-2-pyrrolidone;
   and wherein the pH of said composition is adjusted to a valve in the range of 4.5 to 6.5.

3. The pharmaceutical composition of claim 1 which contains 0.5 to 1.5 mg/g of a lipophilic steroid drug selected from mometasone furoate, betamethasone diproprionate, betamethasone valerate, alcolomethasone diproprionate, hydrocortisone and mixtures thereof.

4. The pharmaceutical composition of claim 1 which contains 5 to 15 mg/g of a lipophilic antifungal drug.

5. The pharmaceutical composition of claim 1 which contains 0.5 to 1.5 mg/g of a lipophilic steroid drug selected from mometasone furoate, betamethasone diproprionate, betamethasone valerate, alcomethasone diproprionate, hydrocortisone and mixtures thereof and 5 to 15 mg/g of a lipophilic antifungal drug.

6. The pharmaceutical composition of claim 2 which contains 0.5 to 1.5 mg/g of a lipophilic steroid drug selected from mometasone furoate, betamethasone diproprionate, betamethasone valerate, alcomethasone diproprionte, hydrocortisone and mixtures thereof.

7. The pharmaceutical composition of claim 2 which contains 5 to 15 mg/g of a lipophilic antifungal drug.

8. The pharmaceutical composition of claim 2 which contains 0.5 to 1.5 mg/g of a lipophilic steroid drug selected from mometasone furoate, betamethasone diproprionate, betamethasone valerate, alcomethasone diproprionate, hydrocortisone and mixtures thereof and 5 to 15 mg/g of a lipophilic antifungal drug.

9. A topical cream pharmaceutical composition of claim 1, which comprises:
   a. 0.5 to 2.0 mg/g of at least one lipophilic steroid or antifungal drug;
   b. 35 mg/g of diethyl sebacate or mineral oil;
   c. 150 mg/g of white petrolatum;

d. 40 mg/g of propylene glycol stearate;
e. 55 mg/g of a mixture of stearyl alcohol and Ceteareth-20;
f. 10 mg/g of trimethylsiloxy-silicate;
g. 50 mg/g of propylene glycol;
h. 10 mg/g of benzyl alcohol; and
i. 50 mg/g of N-methyl-2-pyrrolidone;
j. q.s. of purified water to 1 g; and wherein the pH of said composition is adjusted to a value in the range of 4.5 to 6.5.

10. A topical lotion pharmaceutical composition of claim 2 which comprises:

a. 0.5 to 2.0 mg/g of at least one lipophilic steroid or antifungal drug;
b. 35 mg/g of diethyl sebacate or mineral oil;
c. 100 mg/g of white petrolatum;
d. 25 mg/g of propylene glycol stearate;
e. 25 mg/g of a mixture of stearyl alcohol and Ceteareth-20;
f. 10 mg/g of trimethylsiloxy-silicate;
g. 50 mg/g of propylene glycol;
h. 10 mg/g of benzyl alcohol; and
i. 50 mg/g of N-methyl-2-pyrrolidone
j. q.s. mg/g of purified water to 1 g; and wherein the pH of said composition is adjusted to a valve in the range of 4.5 to 6.5.

* * * * *